United States Patent [19]

Britton et al.

[11] 4,286,090
[45] Aug. 25, 1981

[54] NOVEL TETRAZOLO [4,5-C][1,2,3]BENZOTRIAZINES

[75] Inventors: Thomas C. Britton, Portage, Mich.; Eugene R. Wagner, Carmel, Ind.

[73] Assignee: The Dow Chemical Company, Midland, Mich.

[21] Appl. No.: 121,758

[22] Filed: Feb. 15, 1980

[51] Int. Cl.$^3$ ............................................ C07D 487/04
[52] U.S. Cl. ...................................................... 544/184
[58] Field of Search ......................................... 544/184

[56] References Cited
U.S. PATENT DOCUMENTS 3,389,137  6/1968  Mosby et al. ..................... 260/256.4
3,835,138  9/1974  Wagner ............................. 260/256.4
3,838,126  9/1974  Wagner ............................. 260/256.4

OTHER PUBLICATIONS

Stolle et al., J. Prakt. Chem., vol. 135, pp. 128–136 (1932).

Primary Examiner—John M. Ford

[57] ABSTRACT

Tetrazolobenzotriazine compounds such as 7-chlorotetrazolo[4,5-C][1,2,3]benzotriazine are prepared by the reaction of the corresponding substituted 5-(2-aminophenyl)tetrazole with nitrous acid. These new compounds are useful as initiating explosives, propellants, and chemical blowing agents.

4 Claims, No Drawings

NOVEL TETRAZOLO [4,5-C][1,2,3]BENZOTRIAZINES

BACKGROUND OF THE INVENTION

This invention is directed to new chemical compounds having a high proportion of nitrogen in their molecular structure. It is known that 5-(2-aminophenyl)-tetrazoles react with an aldehyde or ketone or with phosgene to produce 5,6-dihydrotetrazolo(1,5-C)quinazolines and tetrazolo(1,5-C)quinazolin-5(6H)one compounds respectively. The preparation and utility of these compounds as bronchodilators are described in U.S. Pat. Nos. 3,835,138 and 3,838,126. Other tetrazolo compounds of somewhat similar structure are described in U.S. Pat. No. 3,389,137.

SUMMARY OF THE INVENTION

This invention relates to certain tetrazolobenzotriazine compounds, more particularly, compounds of the formula

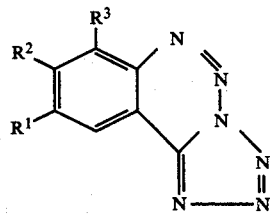

wherein each of $R^1$, $R^2$, and $R^3$ independently represent hydrogen, lower alkyl, lower alkoxy, halo, trihalomethyl, or nitro. The terms lower alkyl and lower alkoxy refer to such groups having 1–3 carbon atoms and halo refers to fluoro, chloro, and bromo.

DETAILED DESCRIPTION OF THE INVENTION

The tetrazolobenzotriazine compounds defined by the above formula decompose explosively when subjected to heat such as produced by electrical discharge, by physical impact or shock, or by direct heating. Consequently they are useful initiating explosives, propellants, and chemical blowing agents. The compounds are crystalline solids, often somewhat colored, depending on the ring substituents.

The compounds of the invention are prepared by the reaction of nitrous acid with a 5-(2-aminophenyl)tetrazole of the formula

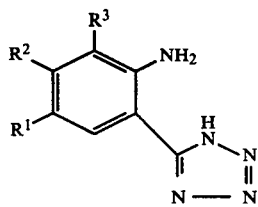

wherein $R^1$, $R^2$, and $R^3$ represent the substituents defined above. These tetrazoles can be prepared by the reaction of a corresponding anthranilonitrile with sodium azide and ammonium chloride, by the method of Finnegan et al., *J. Am. Chem. Soc.*, 80, 3908 (1958) with the addition of lithium chloride, according to Holland et al., *J. Med. Chem.*, 10, 149 (1967). The anthranilonitriles can be prepared by known methods, see McKee et al., *J. Am. Chem. Soc.*, 68, 1902 (1946) and 69, 940 (1947), also Keffler, *J. Chem. Soc.*, 119, 1476 (1921).

The reaction with nitrous acid is conveniently accomplished by slow addition of an aqueous solution of a small excess of sodium nitrite to an ice bath-cooled mixture of the aminophenyltetrazole, aqueous HCl, and ethanol. After stirring the resulting reaction mixture at that temperature for about 1–3 hours, the mixture is made basic by addition of $NaHCO_3$ or $Na_2CO_3$ and the tetrazolobenzotriazine product is isolated by solvent extraction using a water-immiscible organic solvent of low boiling point such as $CHCl_3$. The product can then be obtained as a solid by evaporation of the solvent extract and further purified, if desired, by recrystallization or other suitable standard procedure.

EXAMPLE 1

Tetrazolo[4,5-C][1,2,3]benzotriazine

To a stirred, ice-cooled mixture of 1 g (6.2 mmoles) of 5-(2-aminophenyl)tetrazole, 2 ml of concentrated HCl, 15 ml of water, and 5 ml absolute ethyl alcohol there was added dropwise a solution of 0.47 g (6.81 mmoles) of $NaNO_2$ in 5 ml of water. After the addition was complete, the mixture was stirred at ice bath temperature for 2 hours. The reaction mixture was made basic with aqueous $Na_2CO_3$ and then was extracted with three portions of $CHCl_3$. The combined chloroform extracts were dried over anhydrous $Na_2SO_4$ and concentrated under reduced pressure on a rotary evaporator. The solid residue was washed with hexane and air dried to yield 0.55 g of a cream colored solid identified by infrared and elemental analyses as tetrazolo[4,5-C][1,2,3]benzotriazine. Thin layer chromatographic analysis of the product indicated that it was essentially a pure compound containing only a trace of impurities. This compound exploded when heated to about 120° C.

EXAMPLE 2

7-Chlorotetrazolo[4,5-C][1,2,3]benzotriazine

This compound was prepared from 1 g of 5-(2-amino-3-chlorophenyl)tetrazole, 0.45 g of $NaNO_2$, and concentrated HCl by the procedure described in Example 1. The reaction mixture was made basic with aqueous $NaHCO_3$ and extracted with chloroform as before. The combined and dried extracts were concentrated under a stream of nitrogen at room temperature. The residue was washed with hexane and air dried to yield 0.85 g of a cream colored solid identified by thin layer chromatographic analysis and infrared absorption analyses as the essentially pure compound 7-chlorotetrazolo[4,5-C][1,2,3]benzotriazine.

EXAMPLE 3

8-Methoxytetrazolo[4,5-C][1,2,3]benzotriazine

The above-named compound was prepared from 1 g of 5-(2-amino-4-methoxyphenyl)tetrazole, 0.45 g of $NaNO_2$, and concentrated HCl and isolated from the reaction mixture by the procedures of Example 2. The residue obtained by evaporation of the chloroform extracts was a dark reddish-brown solid shown by liquid chromatographic analysis to be largely the named compound plus several minor impurities. The product was purified by percolating its chloroform solution through two 7–10 ml portions of 80–200 mesh alumina and evaporating the treated solution under nitrogen at room temperature. A yield of 0.54 g of orange solid was obtained. This purified material showed only trace impurities on thin layer chromatographic examination and its structure as the named compound was confirmed by magnetic resonance and infrared absorption analyses.

The shock sensitivities of the products of Examples 1–3 were determined by a standard method consisting of dropping a 1.27 cm diameter steel ball from various heights onto a 0.18 mm coating of the compound on a polished plate of hardened steel. The results of these tests are listed in the table below. Values in the table are the number of fires per number of drops for each compound and height. Unless otherwise specified, a fire was indicated by a star-shaped stain or discoloration on the metal plate caused by decomposition only at the point of impact.

TABLE 1

| Distance Dropped, inches | Compound of | | |
|---|---|---|---|
| | Ex. 1 | Ex. 2 | Ex. 3 |
| 1 | — | — | 0/6 |
| 2 | — | 0/5 | 3/4 |
| 3 | — | 4/12 | 8/8 |
| 4 | 0/4 | 6/9 | 7/8 |
| 5 | 0/4 | 5/5 | — |
| 6 | 2[a]/5 | — | — |

[a] Entire sample coating flashed.

The substituted product compounds of Examples 2 and 3 appear to have somewhat lower decomposition temperatures than that found for the unsubstituted compound of Example 1.

For comparison, the drop heights causing the initial fire and the minimum heights at which all samples showed fires as determined by the same method for three commercial initiating explosives are listed in Table 2. These values were obtained by ten drops at each height.

TABLE 2

| Compound | Initial Fire Height, inches | All Fire Height, inches |
|---|---|---|
| Lead azide | 9 | 38 |
| Lead styphnate | 3 | 11 |
| Tetracene | 1 | 5 |

Other substituted tetrazolobenzotriazines of the general formula shown above are made by the procedure, of the foregoing examples using appropriately substituted 5-(2-aminophenyl)tetrazoles as starting materials. For example, in this way 5-(2-amino-4-chlorophenyl)tetrazole is reacted with nitrous acid to make 8-chlorotetrazolo[4,5-C][1,2,3]benzotriazine; 5-(2-amino-4-methylphenyl)tetrazole is reacted to make 8-methyltetrazolo[4,5-C][1,2,3]benzotriazine; 5-(2-amino-4,5-dimethoxyphenyl)tetrazole is reacted to make 8,9-dimethoxytetrazolo[4,5-C][1,2,3]benzotriazine; 5-(2-amino-5-nitrophenyl)tetrazole is reacted to make 9-nitrotetrazolo[4,5-C][1,2,3]benzotriazine; 5-(2-amino-4,5-dichlorophenyl)tetrazole is reacted to make 8,9-dichlorotetrazolo[4,5-C][1,2,3]benzotriazine; and 5-(2-amino-4-trifluoromethylphenyl)tetrazole is reacted to produce 8-trifluoromethyl)tetrazolo[4,5-C][1,2,3]benzotriazine. These substituted tetrazolobenzotriazine products have explosive properties similar to those of the products of Examples 1–3.

We claim:

1. A tetrazolo[4,5-C][1,2,3]benzotriazine compound of the formula

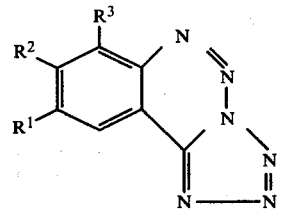

wherein $R^1$, $R^2$, and $R^3$ independently represent hydrogen, lower alkyl, lower alkoxy, halo, trihalomethyl, or nitro and halo refers to fluoro, chloro, and bromo.

2. The compound of claim 1 wherein $R^1$, $R^2$, and $R^3$ each represent hydrogen and the compound is tetrazolo[4,5-C][1,2,3]benzotriazine.

3. The compound of claim 1 wherein $R^1$ and $R^2$ each represent hydrogen, $R^3$ represents chloro, and the compound is 7-chlorotetrazolo[4,5-C][1,2,3]benzotriazine.

4. The compound of claim 1 wherein $R^1$ and $R^3$ each represent hydrogen, $R^2$ represents methoxy and the compound is 8-methoxytetrazolo[4,5-C][1,2,3]benzotriazine.

* * * * *